United States Patent
Herrmann et al.

(10) Patent No.: US 6,194,223 B1
(45) Date of Patent: Feb. 27, 2001

(54) METHOD FOR THE SIMULTANEOUS DETERMINATION OF BIOMOLECULAR INTERACTIONS BY MEANS OF PLASMON RESONANCE AND FLUORESENCE DETECTION

(75) Inventors: Rupert Herrmann; Peter Sluka, both of Weilheim; Wolfgang Knoll, Mainz; Thorstein Liebermann, Rossdorf, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/058,868

(22) Filed: Apr. 13, 1998

(30) Foreign Application Priority Data

Apr. 14, 1997 (DE) .............................. 197 15 483

(51) Int. Cl.[7] .................................. G01N 33/543
(52) U.S. Cl. .................... 436/518; 356/318; 356/445; 422/82.05; 422/82.08; 422/82.11; 435/287.1; 435/287.2; 435/288.7; 435/808; 436/172; 436/524; 436/525; 436/527; 436/805
(58) Field of Search .................... 436/172, 518, 436/524, 525, 527, 805; 422/82.05, 82.08, 82.11; 435/287.1, 287.2, 288.7, 808; 356/318, 445

(56) References Cited

U.S. PATENT DOCUMENTS 4,775,637 * 10/1988 Sutherland et al. .
4,844,613 * 7/1989 Batchelder et al. ................ 356/318

FOREIGN PATENT DOCUMENTS 0 353 937    7/1989  (EP) .
0 353 937  * 2/1990  (EP) .
WO 88/07202 * 9/1988  (WO) .

OTHER PUBLICATIONS

International Publication No. WO 88/07202, published Sep. 22, 1988.

* cited by examiner

Primary Examiner—Christopher L. Chin
(74) Attorney, Agent, or Firm—Arent Fox Kintner Plotkin & Kahn, PLLC

(57) ABSTRACT

A method for the detection of an analyte is described which is characterized in that the binding of the analyte to a solid phase is determined by the independent analysis of the signals from a plasmon resonance measurement and a fluorescence measurement.

8 Claims, 3 Drawing Sheets

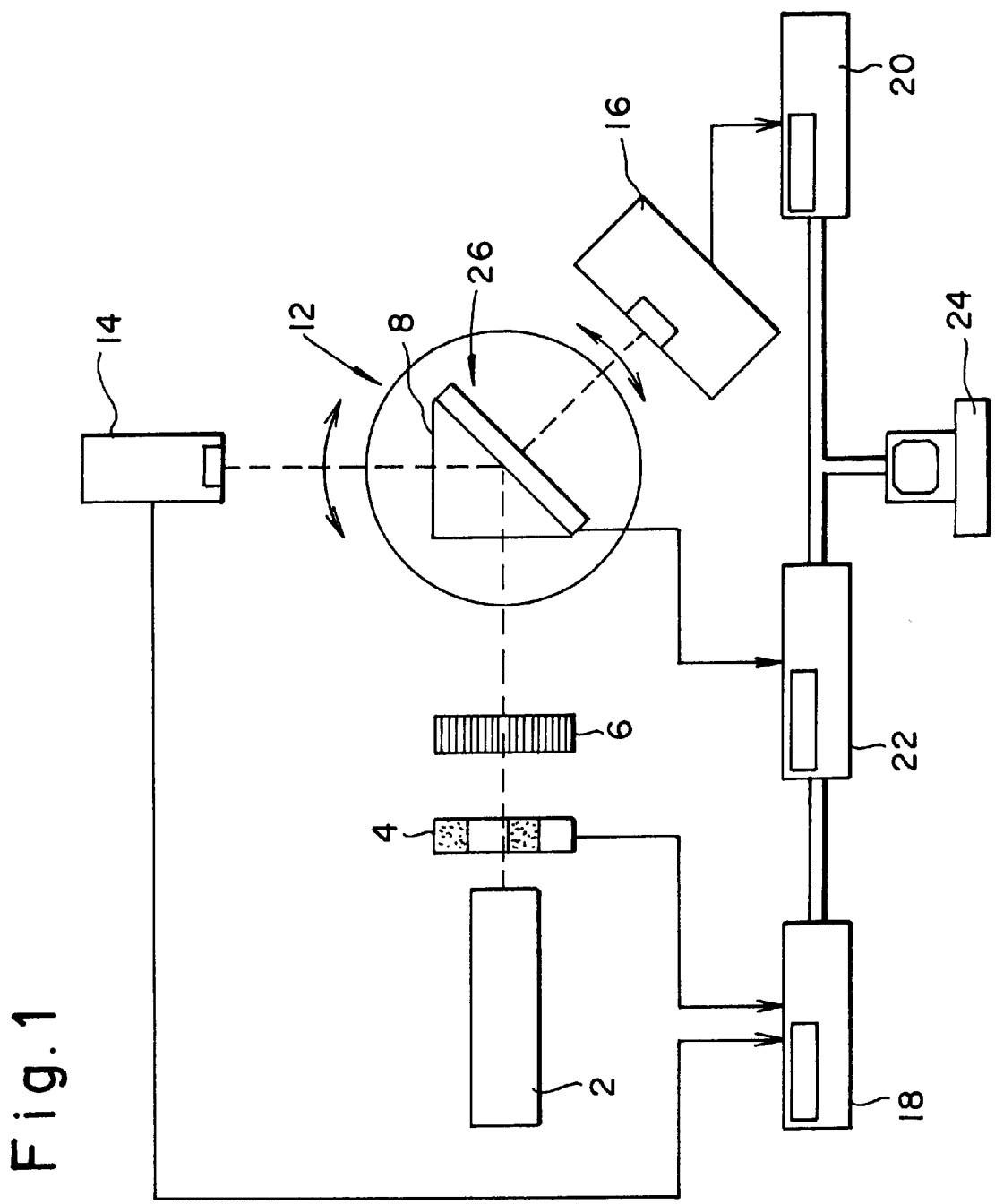

Figure 4:
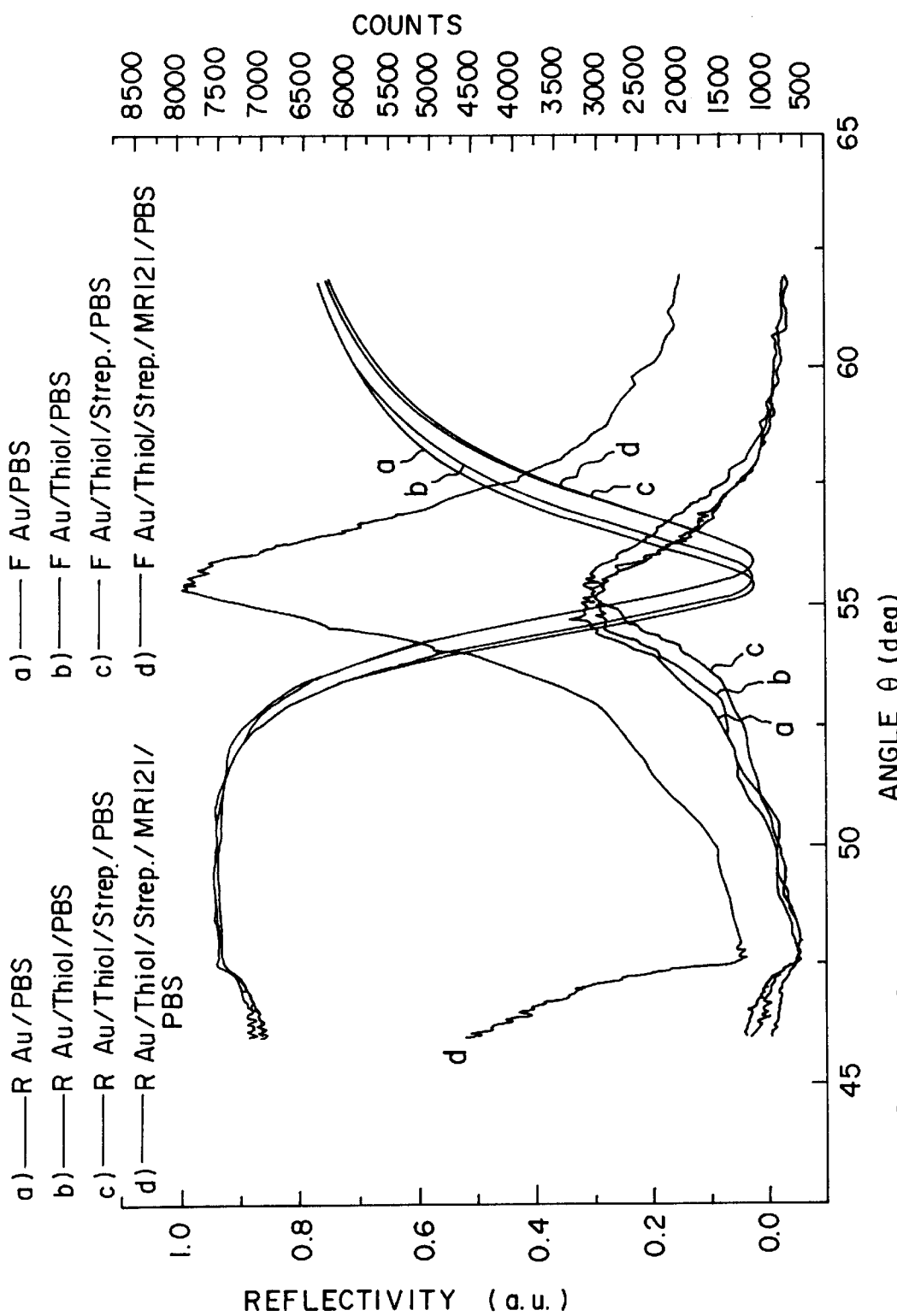

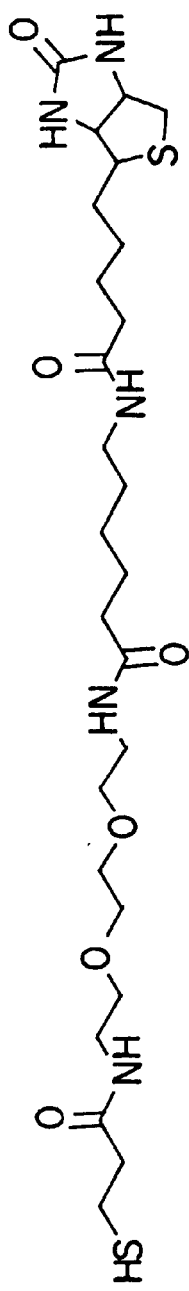
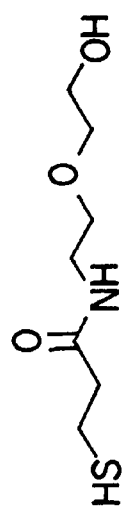
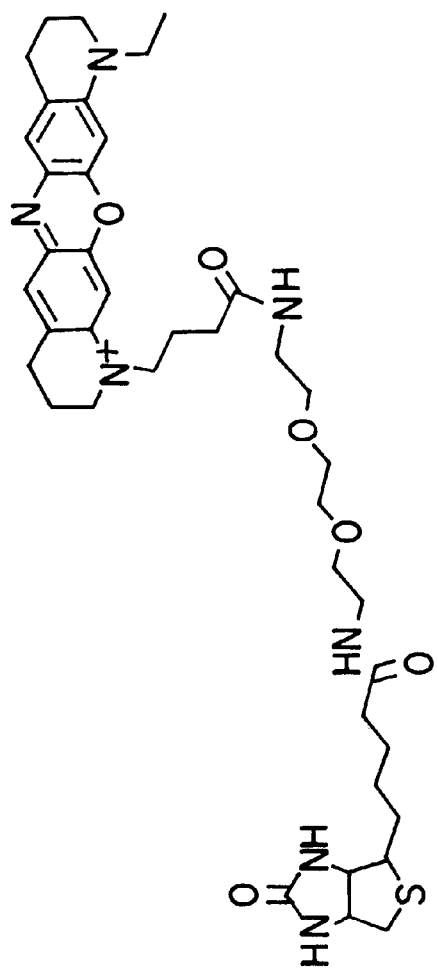
Fig. 2a
Fig. 2b
Fig. 3

METHOD FOR THE SIMULTANEOUS DETERMINATION OF BIOMOLECULAR INTERACTIONS BY MEANS OF PLASMON RESONANCE AND FLUORESENCE DETECTION

The invention concerns a method for the detection of an analyte wherein a combination of plasmon resonance and fluorescence measurement is carried out for the detection and it also concerns a device which is suitable for carrying out this method.

Surface plasmon spectroscopy is used to determine optical layer thicknesses of adsorbed substances on solid phases. No label is required for this detection method and it is possible to carry out so-called real time measurements which enable the determination of the kinetics of reactions of biomolecular interactions and adsorption processes. The disadvantages of surface plasmon resonance are the low sensitivity with a detection limit of about $10^{-10}$ mol/l as well as difficulties and limitations in measuring relatively small molecules.

Fluorescence detection using fluorescent labels is used for example in biochemistry and also in diagnostics. The excitation of fluorescence on surfaces can for example be achieved by an external light source and also by so-called evanescent light. Such excitation of fluorescence by evanescent light takes place for example in the e-wave concept in which the light conducted in a light conductor excites the labels immobilized on the surface of this light conductor to fluoresce (W. F. Love et al., Biosensors and Bioelectronics 7 (1992), 38–48). It is possible to use plasmon light as evanescent light to excite fluorescent labels bound on the surface. The intensity of the evanescent light is several-fold higher than the intensity of the irradiated light so that a considerable increase in the sensitivity of the fluorescence detection can be achieved. Hence the field amplifying effect of surface plasmon resonance is used to increase the fluorescence signal as described for example by Kitson et al., Journal of Modern Optics, vol. 43 (3), (1996), 573–582 and EP-0 353 937. The methods described in these publications are sensitive variants of fluorescence detection which, however, have the disadvantage that kinetic measurements are not possible.

Therefore one object of the present invention was to provide a method which enables an analyte to be detected with high sensitivity and simultaneously allows the determination of reaction kinetics.

This object is achieved according to the invention by a method for the detection of an analyte which is characterized in that the binding of the analyte to a solid phase is determined by independent analysis of the signals from a plasmon resonance and a fluorescence measurement. Surprisingly the method according to the invention enables real time measurements to be carried out while concomitantly achieving a higher sensitivity. According to the invention two independent measurement signals are obtained by the combination of the two methods plasmon resonance detection and fluorescence detection.

An important advantage of the method according to the invention is that plasmon resonance in which the layer thickness is determined also enables the detection of unspecific interactions of the sample containing the analyte with the solid phase whereas fluorescence detection only detects the specific interaction of the analyte with the solid phase. This enables the amount of specific and unspecific binding in a sample to be determined and enables differentiation between both types of binding. Moreover kinetic measurements are additionally possible with plasmon resonance e.g. adsorption can be observed over time whereas end point measurements can be carried out with the fluorescence detection. In this connection a sensitivity of $10^{-13}$ to $10^{-14}$ mol/l is achieved with the fluorescence detection whereas a sensitivity of about $10^{-10}$ mol/l is achieved with the plasmon resonance.

Field amplification by resonant coupling in of the incident light at the reflectivity minimum of the plasmon resonance enables an additional improvement of the sensitivity of the fluorescence detection. This field amplification can be used to excite adsorbed dye molecules as a result of which a surface sensitive detection method is obtained since the evanescent character of the field strength causes a dominant excitation of fluorophores adsorbed to the surface. Since this excitation occurs specifically only for dye molecules bound to the surface it is not necessary to separate dye that is not bound to the surface from bound dye.

The method according to the invention enables the examination of for example biomolecular interactions, reaction kinetics and adsorption processes and also enables analytes to be determined qualitatively or/and quantitatively.

The method according to the invention can be carried out utilizing the intrinsic fluorescence of a reaction partner participating in the detection reaction of an analyte. However, at least one fluorescently labelled reagent is used for the detection.

An optically transparent support which is coated with a metal or metal/metal oxide layer is preferably used as the solid phase for the method according to the invention. The optically transparent support, for example made of glass or quartz glass, can for this purpose be for example vapour-coated with a relatively thin metal or metal/metal oxide layer. The metal/metal oxide layer is in this case preferably composed of a metal layer which is firstly vapour-deposited on the optically transparent support and a metal oxide layer which is subsequently applied onto the metal layer. The thickness of the coating is preferably between 10 nm and 1 $\mu$m particularly preferably between 30 nm and 100 nm. If the support is vapour-coated with a metal layer one preferably uses noble metals and particularly preferably gold or silver. Preferred metal oxide layers include $SiO_2$, $TiO_2$, $Al_2O_3$ and $Ag_2O$.

A solid phase binding matrix via which the analyte is linked to the solid phase is preferably located on the metal or metal oxide layer. A solid phase binding matrix comprises a solid phase reactant which can specifically interact with a binding partner e.g. an analyte to be determined. The solid phase reactant can be covalently or adsorptively linked to the surface via anchor groups, optionally via spacer molecules. The linkage is particularly preferably achieved by means of a self-assembled monolayer (SAM) in which thiol or disulfide groups are adsorptively bound to a metal surface. Such self-assembled monolayers are described for example in DE 40 39 677 the contents of which become part of this application by reference. A dilute and essentially laterally homogeneous binding layer which has particularly advantageous binding properties is preferably formed on the surface of the support material by addition of diluent molecules or by treating a surface with solid phase reactants present in a high dilution. It is, however, also possible to use conventional Langmuir layers as a solid phase binding matrix (Blankenburg et al., Biochemistry 28 (1989) 8214; Ahlers et al., Thin Solid Films 180 (1989) 93–99). Especially suitable silane compounds for application onto metal oxide layers are described in DE 4401450.

A laser which provides monochromatic light is preferably used as a light source for the plasmon resonance and for the fluorescence detection. It is, however, also possible to use other light sources.

The distance between the solid phase surface and the fluorophore used for the fluorescence detection is preferably $\geq 5$ nm, particularly preferably $\geq 20$ nm in order to avoid the metal surface having a disadvantageous influence on the radiated fluorescence. The spacing can for example be achieved by using suitable spacer molecules. The plasmon resonance can be detected in a known manner e.g. by means of a photodiode. The fluorescence can also be detected in any known manner e.g. with a photomultiplier. By using appropriate devices such as for example microscope optics to broaden and parallelize the laser ray and detection via a scanner or CCD camera, it is possible to carry out the method as a combination of plasmon resonance microscopy (A detailed description of plasmon resonance microscopy is given for example by B. Ruthenhäusler et al., Nature, vol. 332 (1988) 615 to 617) and fluorescence detection. Such a method also enables the analysis of array structures i.e. of several reaction zones or spots arranged next to one another on the solid phase. Such an array structure can be used to simultaneously detect several analytes in a sample or/and to simultaneously determine several samples.

A further subject matter of the invention is a device for the detection of an analyte bound to a solid phase which is characterized in that it comprises means for the measurement of the plasmon resonance and the fluorescence and for the independent analysis of the signals from the plasmon resonance measurement and the fluorescence measurement.

Such a device preferably comprises a laser as a light source, a polarizer for p-polarization of the laser light, an optically transparent support which is coated with a metal layer or with a metal oxide layer as a solid phase, a photodiode to detect the plasmon resonance and a photomultiplier for the fluorescence detection. In this case the solid phase particularly preferably comprises a support which is coated over the entire area with a metal or metal/metal oxide layer on which spatially defined reagent spots are applied which contain different solid phase reactants or/and a solid phase reactant in different concentrations. Such a device particularly preferably contains means for carrying out a plasmon resonance microscopy measurement and a fluorescence measurement and means for the independent analysis of the signals from the plasmon resonance microscopy measurement and the fluorescence measurement.

The invention in addition concerns the use of such a device to detect an analyte bound to a solid phase e.g. for carrying out immunoassays or nucleic acid hybridization assays. The invention is further elucidated by the attached figures and the following examples.

FIG. 1 shows the experimental construction of a device according to the invention, FIG. 2 shows reagents which are suitable for forming a self-assembled monolayer, FIG. 2a shows a biotinylated thiol (solid phase reactant) and FIG. 2b shows an OH-terminated thiol (diluent molecule), FIG. 3 shows a biotinylated fluorescent marker and FIG. 4 shows measurements of the reflectivity and fluorescence intensity which were obtained with a device according to the invention.

The construction of a device according to the invention is shown schematically in FIG. 1 and comprises a laser (2), a chopper (4), a polarizer (6), a prism (8), a goniometer (12), a photodiode (14), a photomultiplier (16) as well as the corresponding hardware and software to control and evaluate the measured results comprising a lock in (18), a counter (20), a temperature regulator (22) as well as a PC (24). The construction shown in FIG. 1 enables the simultaneous angle-dependent and time-dependent measurement of the reflectivity (SPR, surface plasmon resonance) and the fluorescence intensity. The surface plasmons in the metal layer (26) are excited by the irradiated light for example by a laser diode at 650 nm or a laser at 543 nm. The continuous laser light ray is divided by the chopper (4) into segments separated in time and is p-polarized by the polarizer (6). The p-polarized laser light impinges on a glass prism on the reverse side of which a microscope slide is located that is vapour-coated with a ca. 50 nm thick gold layer. The reagents are adsorbed to the gold surface for example by means of a dilute self-assembled monolayer containing the reagents shown in FIG. 2. The light reflected by the sample (plasmon resonance) is measured by the photodiode (14) and by the lock in amplifier (18). The fluorescence intensity is measured concurrently by the photomultiplier (16) with an interference filter in front and a counter (20). The experiment is controlled and the signals are measured by means of a PC (24).

EXAMPLE 1

Production of the Reagent Supports

A ca. 50 nm thick gold layer is vapour-deposited on a glass support made of LASFN9 in a high-vacuum coating apparatus (Leibold Company). Immediately after vapour-coating the gold layer, an alkanethiol layer composed of a mixture of a biotinylated and an OH-terminated thiol is applied by means of a self-assembled adsorption process as shown in FIG. 2. The concentration of the thiols is $10^{-6}$ mol/l in water, the proportion of biotinylated thiol being 10%, the proportion of the OH-terminated thiol being 90%. A streptavidin layer is applied on this layer as a monolayer on the reagent support from a PBS buffer containing a streptavidin concentration of $5 \times 10^{-6}$ mol/l. A support manufactured in this manner can be used directly.

EXAMPLE 2

Measurement of the Adsorption of a Biotinylated Fluorescent Dye

The biotinylated fluorescent dye shown in FIG. 3 is applied from an aqueous solution to a support coated with streptavidin that is produced as in example 2. This dye has an absorption maximum at 464 nm and an emission maximum at 676 nm. An angle-dependent (scan operation) and time-dependent (kinetic operation) measurement of the reflectivity and the fluorescence intensity was carried out simultaneously using the device described in example 1. The surface plasmons were excited by a laser diode with a wavelength of 650 nm and the incident light was p-polarized by a polarizer. The device measured simultaneously the fluorescence intensity by means of a photomultiplier as well as the reflectivity by means of a photodiode.

Firstly an alkanethiol layer was applied to the gold substrate by a self-organized adsorption process as described in example 2. The alkanethiol layer was composed of a binary mixture of biotinylated alkane-thiols as well as OH-terminated thiols. The dilution of the biotinylated thiols served to optimally expose the biotin ligands in order to favour the formation of the subsequently adsorbed streptavidin monolayer. The concentration of the thiols was $10^{-6}$ mol/l in a PBS buffer (0.137 M NaCl, 0.01 M phosphate buffer) and 10 parts by volume of the biotinylated thiol and 90 parts by volume of the OH-terminated thiol were used. This mixing ratio allowed the sterically unhindered formation of a streptavidin monolayer from a streptavidin solution ([SA]=$5 \times 10^{-6}$ M) in PBS buffer. After the preparation of the streptavidin matrix a combined plasmon resonance and fluorescence reference measurement was carried out. This measurement already showed a detectable increase of the fluorescence intensity in the region of the resonance minimum which is due to the intrinsic fluorescence of the layer system (FIG. 4, curves c). Moreover the intensity maximum of the fluorescence followed the shift of the resonance minimum when the thiols and the streptavidin were immobilized as theoretically predicted by Fresnell simulations. Measurements on a gold surface were carried out for comparison on which only the PBS buffer was applied (FIG. 4, curves a) as well as on a gold surface on which a self-assembled monolayer composed of biotinylated alkanethiols as well as OH-terminated thiols but not a streptavidin monolayer was applied (FIG. 4, curves b).

Finally the adsorption of the biotinylated dye was determined by simultaneous fluorescence and reflectivity measurement. For this the biotinylated dye was adsorbed to a surface prepared according to example 2. From the results shown in FIG. 4, curves d it can be seen that the detected fluorescence has a significantly increased signal compared to the background and thus enables the detection of the dye adsorption.

What is claimed is:

1. Method for the detection of an analyte, the method comprising the steps of:

contacting the analyte with a solid phase, said solid phase comprising an optically transparent support coated with a metal layer, to effect a binding of the analyte to the solid phase;

irradiating the analyte and the optically transparent support with a light source;

measuring a resulting plasmon resonance and a resulting fluorescence; and independently analyzing a first signal obtained from the plasmon resonance measurement and a second signal obtained from the fluorescence measurement to detect the binding of the analyte to the solid phase, wherein at least one fluorescent-labeled reagent is used to detect the binding of the analyte to the solid phase.

2. Method as claimed in claim 1, wherein the optically transparent support is coated with a metal/metal oxide layer.

3. Method as claimed in claim 1, wherein the optically transparent support is coated with a silver or gold layer.

4. Method as claimed in claim 1, wherein the binding of the analyte to the solid phase further comprises a solid phase binding matrix.

5. Method as claimed in claim 4, wherein
the solid phase binding matrix comprises a self-assembled monolayer.

6. Method as claimed in claim 1, wherein a laser is used as the light source for the plasmon resonance measurement and for the fluorescence measurement.

7. Method as claimed in claim 1, wherein
the distance between the solid phase surface and the fluorophore used for the fluorescence detection is $\geq 5$ nanometers.

8. Method as claimed in claim 1, wherein the first signal from a plasmon resonance microscopy measurement and the second signal from the fluorescence measurement are used to detect the binding of the analyte to the solid phase.

* * * * *